( 12 ) United States Patent
Deininger et al.

(10) Patent No.: US 10,373,813 B2
(45) Date of Patent: Aug. 6, 2019

(54) NORMALIZATION OF MASS SPECTRA ACQUIRED BY MASS SPECTROMETRIC IMAGING

(71) Applicant: Bruker Daltonik GmbH, Bremen (DE)

(72) Inventors: Soren-Oliver Deininger, Leipzig (DE); Eryk Wolski, Bremen (DE)

( * ) Notice: Subject to any disclaimer, the term of this patent is extended or adjusted under 35 U.S.C. 154(b) by 0 days.

(21) Appl. No.: 15/433,557

(22) Filed: Feb. 15, 2017

(65) Prior Publication Data

US 2017/0221686 A1 Aug. 3, 2017

Related U.S. Application Data

(63) Continuation of application No. 13/110,541, filed on May 18, 2011, now abandoned.

(60) Provisional application No. 61/347,026, filed on May 21, 2010.

(51) Int. Cl.
*H01J 49/00* (2006.01)
*H01J 49/16* (2006.01)
*G01N 33/68* (2006.01)

(52) U.S. Cl.
CPC ...... *H01J 49/0004* (2013.01); *G01N 33/6851* (2013.01); *H01J 49/0036* (2013.01); *H01J 49/164* (2013.01)

(58) Field of Classification Search
CPC .. H01J 49/0004; H01J 49/164; H01J 49/0036; G01N 33/6851
See application file for complete search history.

(56) References Cited

U.S. PATENT DOCUMENTS

| | | | | |
|---|---|---|---|---|
| 2004/0228846 A1* | 11/2004 | Pang | ...................... | A61K 38/22 424/93.7 |
| 2005/0059013 A1* | 3/2005 | Chan | ................ | G01N 33/57449 435/6.12 |
| 2008/0107649 A1* | 5/2008 | Zurbriggen | ........ | C07K 14/4711 424/133.1 |
| 2010/0191541 A1* | 7/2010 | Prokoski | .............. | A61B 5/0064 705/2 |
| 2011/0315871 A1* | 12/2011 | Komatsu | ............ | G01N 33/6848 250/282 |
| 2012/0085903 A1* | 4/2012 | Trimpin | ................ | H01J 49/044 250/282 |

OTHER PUBLICATIONS

Albrethsen "Reproducibility in Protein Profiling by MALDI-TOF Mass Spectrometry," Clinical Chemistry 53:5, 2007, 852-858.*
Norris et al. "Proceeding MALDI Mass Spectra to Improve Spectral Direct Tissue Analysis," Int, J. Mass Spectrum, Feb. 1, 2007:260 (2-3): 212-221.*

* cited by examiner

*Primary Examiner* — Janet L Suglo
*Assistant Examiner* — Liam R Casey
(74) *Attorney, Agent, or Firm* — Benoit & Côté Inc.

(57) ABSTRACT

Mass spectra acquired by imaging mass spectrometry (IMS), in particular MALDI imaging of tissue sections, are each normalized by one of: the p-norm of the mass spectrum transformed by applying an exclusion list, the p-norm of the mass spectrum transformed by square rooting the intensity values, the median of the mass spectrum, and the median absolute deviation of the noise level of the mass spectrum.

10 Claims, 11 Drawing Sheets

No normalization
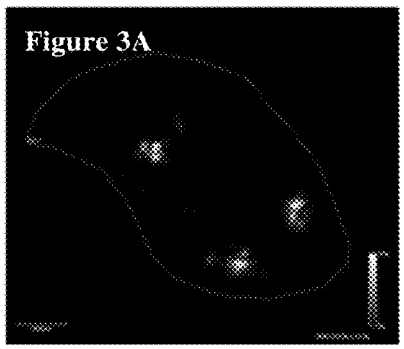
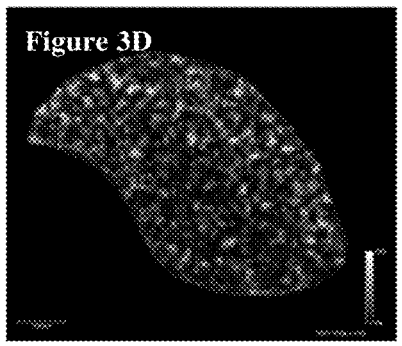
Normalization on vector norm
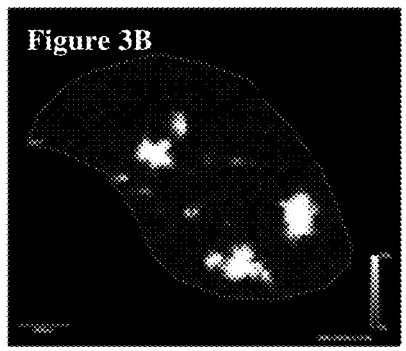
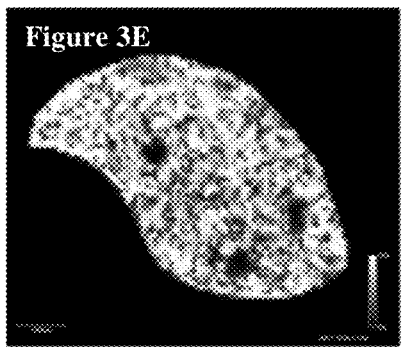
Normalization on TIC
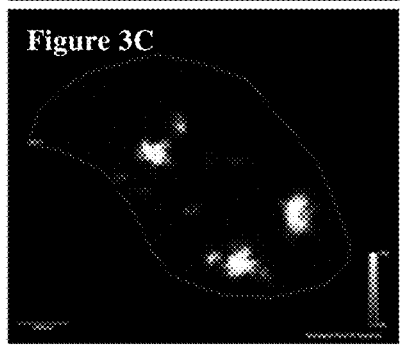
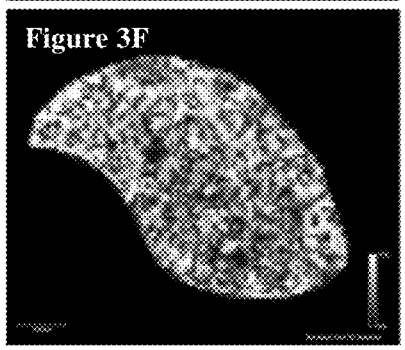
(prior art)

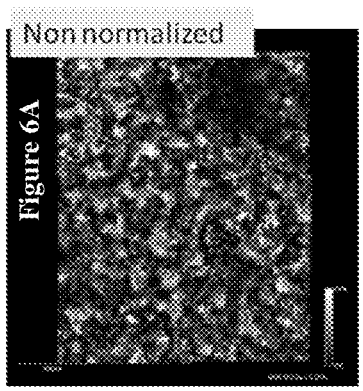 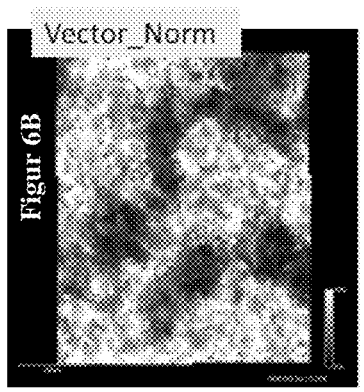 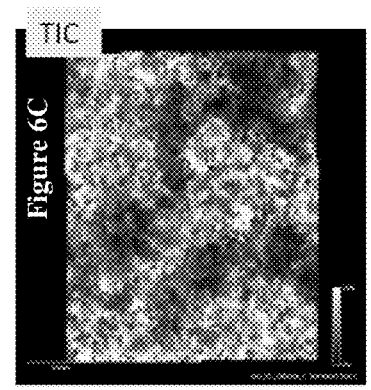
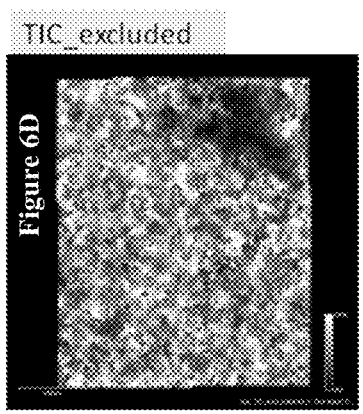 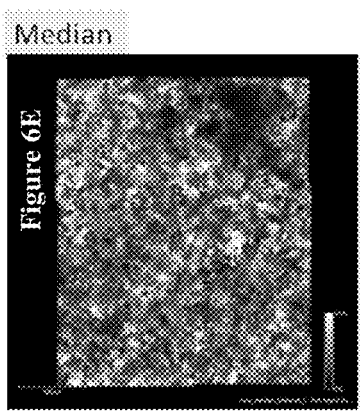 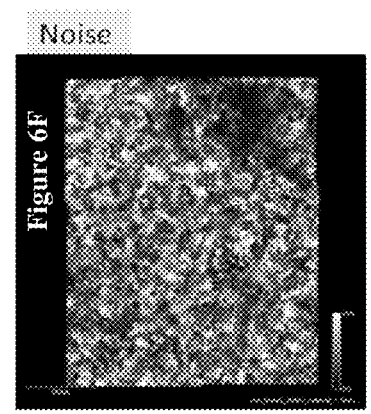

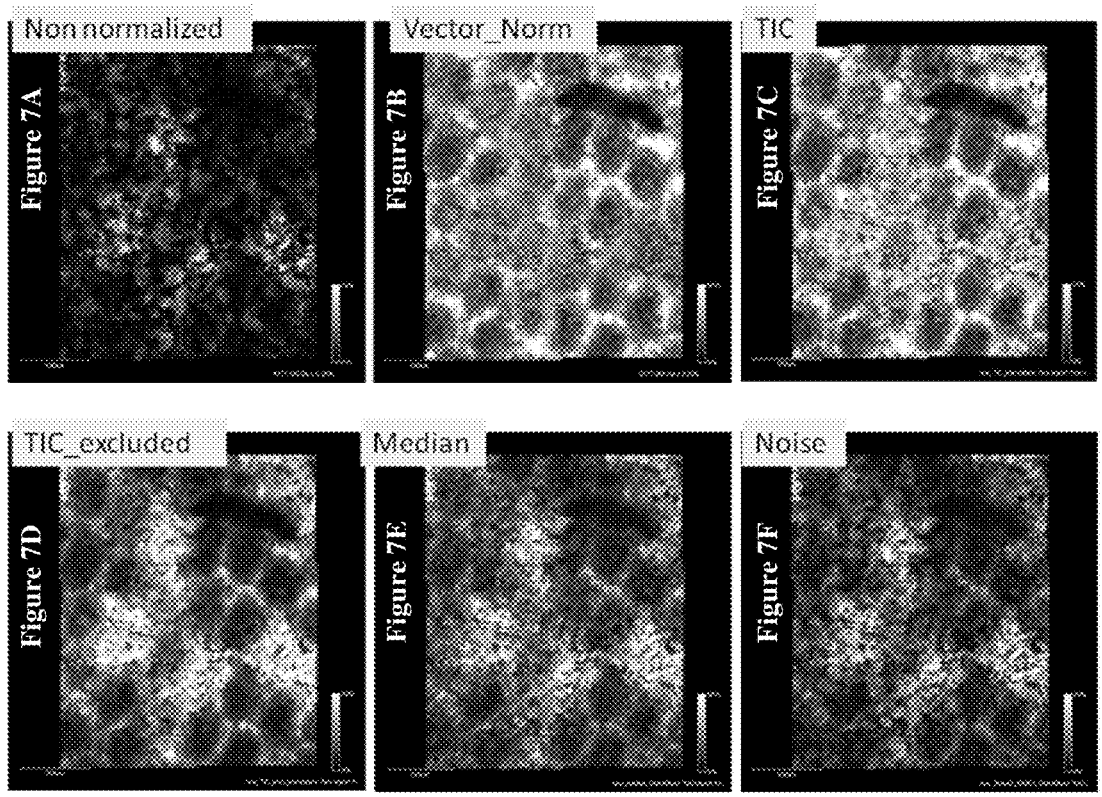

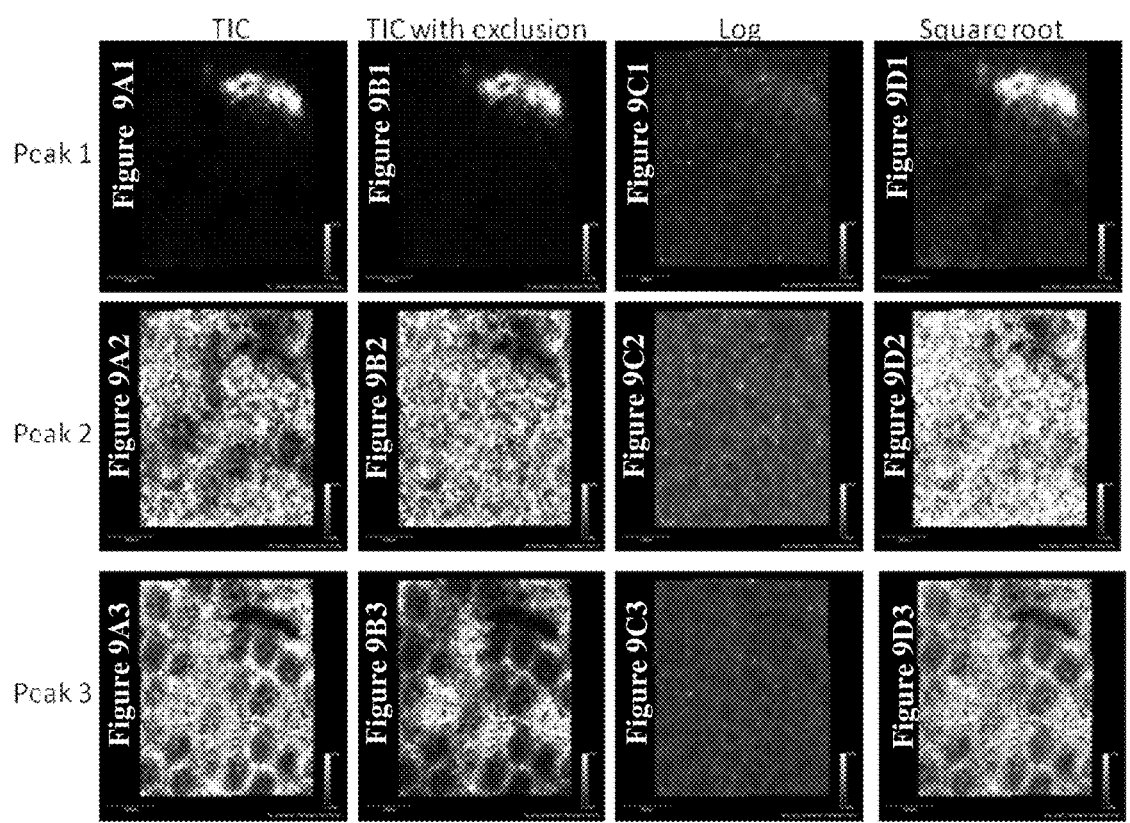

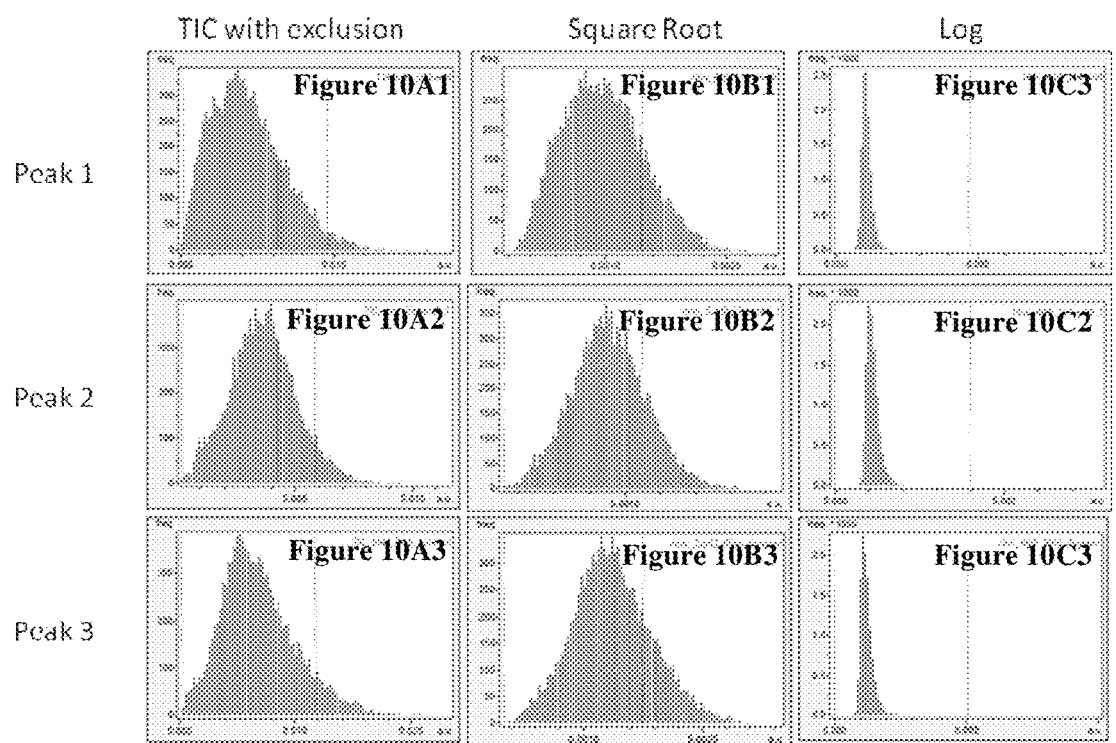

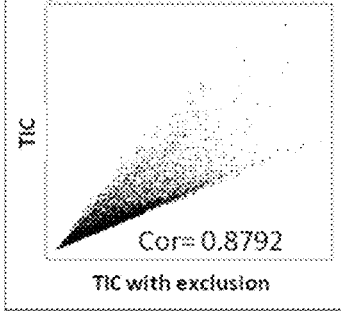
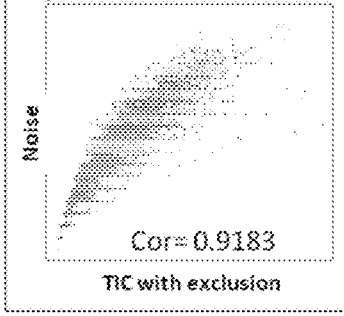
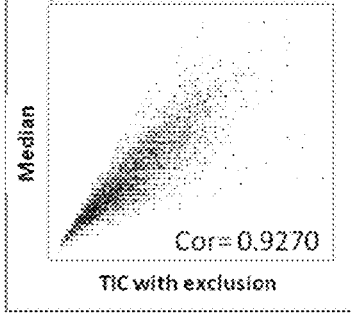
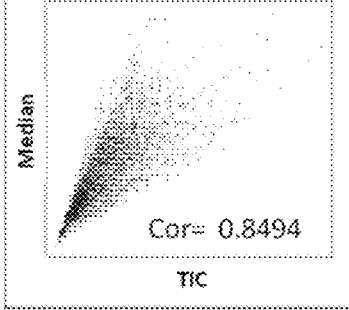
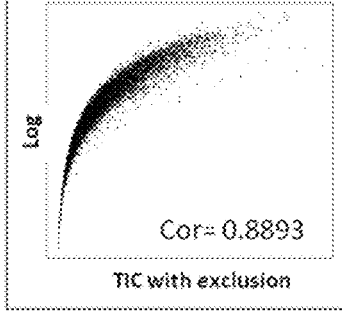
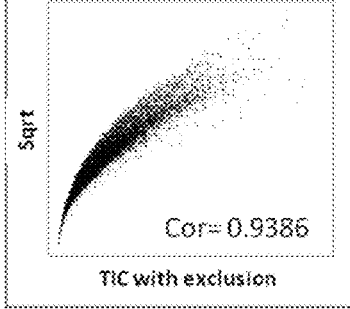

NORMALIZATION OF MASS SPECTRA ACQUIRED BY MASS SPECTROMETRIC IMAGING

BACKGROUND

The invention provides methods for normalizing mass spectra acquired by imaging mass spectrometry (IMS), particularly by imaging tissue sections using matrix assisted laser desorption/ionization (MALDI). Histology is the science of human, animal and plant tissues, in particular, their structure and function. A histologic examination of a tissue sample determines the kind and state of the tissue, e.g. the type(s) and differentiations of the tissue sample, bacterial and parasitic pathogens in the tissue sample, the disease state of the tissue sample or any other change compared to a normal state.

In routine examination, the kind and state of a tissue sample are determined by optically imaging tissue sections, acquired by microscopes or scanners. Usually, the tissue sections are only a few micrometers thick and are stained to increase the contrast of the optical images and emphasize structures in the tissue sections. Histology has mainly been based on morphologic characteristics since the kind and state of a tissue sample are determined according to the presence of specific structures of tissue and cells and their staining properties.

Imaging mass spectrometry (IMS) is a technique used to determine (and visualize) the spatial distribution of compounds in a sample by acquiring spatially resolved mass spectra. In recent years, IMS is increasingly used to analyze the spatial distributions of compounds in tissue sections (Caprioli; U.S. Pat. No. 5,808,300 A), particularly by using matrix assisted laser desorption/ionization (MALDI). However, IMS can also be used to analyze other types of samples, like plates of thin layer chromatography (Maier-Posner; U.S. Pat. No. 6,414,306 B1), gels of an electrophoresis or blot membranes. All spatially resolved mass spectra of a sample constitute a mass spectrometric imaging data set $S(x,y,m)$. The mass spectrometric imaging data set $S(x,y,m)$ of a sample can be viewed as a collection of multiple mass images $S(x,y,m_k)$ of different masses or mass ranges $m_k$, that is, $S(x,y,m)$ can be divided into mass ranges each generating a mass image.

Caprioli has established a raster scan method to acquire spatially resolved MALDI mass spectra of tissue sections. A tissue section is prepared on a sample plate with a matrix layer and then scanned with laser pulses of a focused laser beam in the x- and y-directions, often with several hundred pixels in both directions. In order to raster an entire tissue section, the sample plate is moved by a stage along the x- and y-direction. Every pixel (focus region of the laser beam) on the tissue section is irradiated at least once in the imaging process, and usually ten to a hundred times. The ions generated in the multiple MALDI processes are analyzed in a mass analyzer, most often a time-of-flight mass spectrometer with axial ion injection. The multiple mass spectra acquired at a single pixel are added to a sum spectrum and the sum spectrum is assigned to the pixel.

If the concentrations of compounds are sufficiently high in the tissue section, the spatial distribution can be determined by IMS. The tissue section is characterized by the spatial distribution of compounds, i.e. by molecular information. The compounds can be all kinds of biological substances, like proteins, nucleic acids, lipids and sugars, or drugs. Chemical modifications of compounds, in particular post-translational modifications of proteins and metabolites of drugs, can be determined across the tissue section. In general, IMS generates spatially resolved mass spectra and thus provides high content molecular information as well as morphologic information, the latter at a limited spatial resolution compared with the optical images.

According to Suckau et al. (U.S. Pat. No. 7,873,478 B2), the spatial distribution of a tissue kind and state can be determined by combining at least two different mass signals at each pixel with predetermined mathematical or logical expressions to generate a measure representing the tissue kind and state at that spot. The different mass signals represent different compounds, i.e., that two or more different mass images are combined with predetermined mathematical or logical expressions to a state image of the tissue section. The state image is often displayed together with an optical image of the tissue section.

Normalization is the process of multiplying (or dividing) a mass spectrum with an intensity-scaling factor (normalization factor f) to expand or reduce the range of the intensity axis. It is used to compare mass spectra of varying intensity (Baggerly 2003, Morris 2005, Norris 2007, Smith 2006, Villanueva 2005, Wagner 2003, Wolski 2006, Wu 2003; see list at the end of the disclosure). In general, a mass spectrum S is a vector of multiple intensity values $s_i$ (i=1 ... N) at corresponding masses $m_i$. The mass spectrum S is multiplied or divided by the normalization factor to generate a normalized mass spectrum.

Intrinsic properties of a tissue and the preparation of a tissue section for MALDI imaging may influence the normalization of the acquired mass spectra and can lead to artifacts in normalized mass images. For example, an inhomogeneous spatial distribution of salts or endogenous compounds can suppress the formation of ions in the MALDI process and lead to an inhomogeneous mass image of a compound that is homogeneously distributed in the tissue section. The mass signals of lipids being present in the tissue can be much more intense than signals of peptides or proteins. Therefore, there is risk that highly concentrated lipids suppress the formation of peptide and protein ions.

Further, MALDI imaging requires the preparation of a matrix layer on the tissue section. The properties of the matrix layer, particularly the size of matrix crystals and their spatial distribution on the tissue section, can affect mass signals of compounds, like proteins, irrespective of their concentration in the tissue section. That is of interest since the resolution of a MALDI mass image can actually be higher than the size of the matrix crystals. A contamination of the MALDI ion source can fade the image brightness during the acquisition of the entire MALDI imaging data set.

Besides using an optimized and stable preparation, the influence of the tissue and its preparation on mass images can be minimized by proper normalization. A failure to apply normalization can also lead to artifacts in mass images. A normalization is also required to compare mass spectra across different imaging data sets in cohort studies, e.g., for biomarker discovery.

The most commonly used normalization procedures in mass spectrometry are normalization on the total ion count (TIC) as well as the vector norm. The TIC-norm and the vector norm are special cases of the so called p-norm of a mass spectrum S:

$$\|S\| = \left(\sum_i s_i^p\right)^{1/p}$$

For p=1, the normalization is based on the sum of all intensity values $s_i$ in the mass spectrum S, which is equal to the total ion count (TIC). The TIC-normalized mass spectra have the same integrated area under the spectrum. The normalization factor of the TIC norm is:

$$f_{TIC} = \sum_i |s_i|$$

For p=2, the p-norm equals the vector norm. The normalization factor of the vector norm is:

$$f_{vector} = \sqrt{\sum_i S_i^2}$$

For p→∞, the p-norm leads to the maximum norm, in which the normalization is done on the most intensive peak of the mass spectrum (and which is sometimes used in LC-MS based label-free approaches). The larger the exponent p becomes, the higher the influence of intensity signals on the result of the normalization becomes. This is also true for noise spectra. In the maximum norm, the highest intensity value in a noise spectrum will be the same as the highest intensity pixel of the most intense signal of other spectra. Noise spectra are therefore considerably amplified by increased p, and are therefore expected to be least problematic in TIC normalization.

The TIC-normalization and the vector norm as well are based on the assumption that a comparable number of signals is present with more or less similar intensities in all mass spectra to be normalized. This assumption is fulfilled for samples, like serum samples or homogenized tissue samples, where only a few signal intensities change against an otherwise constant background. In mass spectrometric imaging data sets, one cannot trust that this condition is met because different types of tissue (or cells) may be present in the same tissue section. As a consequence, it is possible to compare expression levels across samples for comparable types of tissue after TIC normalization. However, the error can be high when comparing expression levels between different types of tissue expressing a heterogeneous set of compounds with quite different spatial distributions. In certain cases, the TIC normalization can produce misleading results and possibly lead to wrong conclusions, e.g., regarding the spatial distribution of a potential biomarker, drug or metabolite of a drug. This is typical for tissues in which abundant signals are present in confined areas, such as insulin in the pancreas or beta-amyloid peptides in the brain. The question of whether or not MALDI imaging datasets should be normalized, and the optimal model to do so, is still subject of intense debate at conferences or MALDI imaging workshops.

In principle, every mass spectrometer analyzes ions according to the ratio of their mass to the number of their unbalanced elementary charges (m/z, also termed the "charge-related mass"). Since MALDI is of particular importance for acquiring spatially resolved mass spectra and provides only singly charged ions, the term "mass" rather than "charge-related mass" will be used below only for the sake of simplification. Spatially resolved mass spectra of mass spectrometric imaging data sets can be acquired with different kinds of mass spectrometers. At present, time-of-flight mass spectrometers (TOF-MS) with axial ion injection are mainly used for MALDI imaging, but time-of-flight mass spectrometers with orthogonal ion injection, ion traps (electrostatic or high frequency) or ion cyclotron resonance mass spectrometers can also be used therefore.

SUMMARY

In accordance with the principles of the invention mass spectra of a mass spectrometric imaging data set are normalized in a variety of methods and used to derive mass images which are displayed or used for a further analysis. Each mass spectrum is normalized by the p-norm of that mass spectrum. However, before the p-norm is calculated, the spectrum is transformed in a predetermined manner. The p-norm is most preferably the TIC (total ion count) of the mass spectrum, but can be other normalization functions.

In one embodiment, the mass spectrum is transformed by applying an exclusion list before the p-norm is calculated.

In another embodiment, the mass spectrum is transformed by square rooting the intensity values (square root intensity transformation) before the p-norm is calculated.

In still another embodiment, the mass spectrum is transformed by the median of the mass spectrum.

In yet another embodiment, the mass spectrum is transformed by the median absolute deviation of the noise level of the mass spectrum.

In this process, mass spectra of the mass spectrometric imaging data set are preferably acquired by MALDI imaging. The samples analyzed by MALDI imaging are preferably tissue sections, but can also be plates of thin layer chromatography, gels of an electrophoresis or blot membranes. The mass spectrometric data set and thus mass images derived from the data set can cover the entire sample or one or more regions of interest which can be predetermined or selected by a user. The mass spectra to be normalized can be any subset of the mass spectra of a mass spectrometric imaging data set, e.g. every second mass spectrum in one or both directions, or can be derived from the mass spectra of a mass spectrometric imaging data set, e.g. by binning.

The artifacts introduced to mass images of a tissue section by the TIC norm or the vector norm are usually a result of mass signals with high intensity or large areas under the peak in confined regions on the tissue section. These mass signals are preferably incorporated into the exclusion list so that they do not affect the subsequent p-normalization. The intensity values of the mass spectrum $S(x_i,y_j,m)$ at pixel $(x_i,y_j)$ are transformed by applying the exclusion list to the mass spectrum; then the normalization factor f exclusion is calculated from the transformed mass spectrum $\bar{S}(x_i,y_j,m)$:

$$\bar{S}(x_i, y_j, m) = \begin{cases} 0, & m_{lower} < m < m_{higher} \\ S(x_i, y_j, m), & \text{else} \end{cases},$$

wherein $m_{lower}$ and $m_{higher}$ define the boundaries of a single mass range. The exclusion list can in principle comprise two or more mass ranges $M_n$:

$$\bar{S}(x_i, y_j, m) = \begin{cases} 0, & m \in M_1 \vee M_2 \vee \ldots M_n \\ S(x_i, y_j, m), & \text{else} \end{cases}$$

The normalization factor $f_{exclusion}$ is equal to: $f_{exclusion}=\|\overline{S}\|$ The mass spectra S are preferably normalized by the total ion count of the transformed mass spectrum $\overline{S}$. The exclusion list can be defined by a user after an inspection of mass images normalized by the TIC without an exclusion list in order to identify one or more mass ranges of signals that lead to artifacts. The user may start from an empty list or a predetermined exclusion list and iteratively add (or remove) mass ranges to the exclusion list. The mass ranges can be predetermined depending on the kind of tissue.

Normalization does not have to be based on the peak areas or maximum intensities of the mass signals, but can be also based on the noise level $n_i$ of a mass spectrum. A normalization factor $f_{noise}$ can for example be calculated by the median absolute deviation of the noise level:

$$f_{noise}=\text{median}(|n_i-\text{median}(n_i)|)$$

There are different ways to estimate the noise level $n_i$ of a mass spectrum. Wavelet shrinkage, a signal de-noising technique, is frequently used to smooth and denoise chromatograms and mass spectra. It employs the universal thresholding method to derive an estimate of the noise level in a spectrum. In this method, the noise level $n_i$ is estimated from the detail coefficients $d_i$ of the finest scale. The detail coefficients $d_i$ of the finest scale can be determined without computing a complete wavelet decomposition. In case of the Haar wavelet decomposition, the detail coefficients $d_i$ are differences of consecutive intensity values $s_i$ of the mass spectrum S:

$$d_i=s_i-s_{i-1},$$

and the normalization factor $f_{noise}$ is: $f_{noise}=\text{median}(|d_i-\text{median}(d_i)|)$ The calculation of the noise level $n_i$ can be affected by operations like smoothing and especially binning, which are often part of a MALDI imaging workflow. Normalization can also be based on the median of the mass spectrum which shall be robust to these preprocessing methods and is expected to be a measure for the intensity of the baseline. Therefore, the normalization factor $f_{median}$ is calculated by the median of the intensities values $s_i$ of a measured mass spectrum S:

$$f_{median}=\text{median}(s_i)$$

Using both latter approaches it is possible to circumvent the inherent dangers of the TIC normalization without the need of a user intervention to provide an exclusion list.

In a second embodiment, the invention provides a method for normalizing mass spectra of a mass spectrometric imaging data set, wherein a first mass image is derived from the normalized mass spectra according to the first aspect of the invention, each mass spectrum is additionally normalized by a p-norm (preferably by the total ion count without applying the exclusion list, a second normalized mass image is derived from the additionally normalized mass spectra, the additionally normalized mass spectra are used, if the first and second normalized images are substantially similar.

The mass images can be compared by a user in order to determine the similarity between them. A similarity comparison can also be performed by known image comparison algorithms for the entire images or only for one or more regions of interest, e.g. by correlating the entire images or corresponding regions, by comparing coefficients of a Fourier transform or wavelet transform or by calculating and comparing statistical characteristics (mean, median, variance). The regions of interest used for the comparison can be overlapping or disjoint.

In a third embodiment, the invention provides a method for normalizing mass spectra of a mass spectrometric imaging data set, comprising the steps:
(a) calculating first normalization factors for each mass spectrum by one of: the p-norm of the mass spectrum transformed by applying an exclusion list, the p-norm of the mass spectrum transformed by square rooting the intensity values (square root intensity transformation), the median of the mass spectrum, and the median absolute deviation of the noise level of the mass spectrum,
(b) calculating second normalization factors for each mass spectrum by a p-norm without an exclusion list, and
(c) normalizing the mass spectra by the corresponding second normalization factors, if the first and second normalization factors match in a statistical test, and otherwise by the corresponding first normalization factors.

The p-norm in steps (a) and (b) is most preferably the total ion count of the mass spectrum. In a preferred embodiment, the statistical test is a correlation, e.g. a Pearson correlation. The normalization factors match if the correlation coefficient is preferably greater than 0.8, more preferably greater than 0.9 for increased certainty. In another embodiment, the statistical test is a chi-square analysis of the distributions of the calculated normalization factors.

The methods according to the invention can be used to determine and visualize the spatial distribution of compounds in a tissue. At first, a mass spectrometric imaging data set of a tissue section is acquired. At second, the mass spectra of mass spectrometric imaging data are normalized by a method according to the invention. At third, a mass image is derived from the normalized mass spectra and displayed.

BRIEF DESCRIPTION OF THE DRAWINGS

FIG. 1A shows an optical image of the unstained tissue section prior to the measurement. FIG. 1B shows an optical image of the matrix distribution after preparation. FIG. 1C shows a mass image of a selected mass signal without normalization. FIG. 1D is an overlay of FIGS. 1B and 1C. FIG. 1E shows a mass image of the selected mass signal after normalization by the vector norm.

FIGS. 3A to 3F show mass images of a mouse pancreas for insulin (FIGS. 3A to 3C) and a housekeeping protein in the pancreas (FIGS. 3D to 3F) with no normalization, normalization on vector norm and normalization on the total ion count (TIC).

FIGS. 6A to 6F show mass images of a compound that is homogeneously distributed in the rat testis applying different normalizations.

FIGS. 7A to 7F show mass images of a compound that is only present in certain tubuli of the rat testis after applying different normalizations.

FIGS. 9A1 to 9D3 show mass images of three different compounds of the rat testis (peak 1, peak 2 and peak 3) after applying the TIC-norm (Figures Ax), the TIC-norm with an exclusion list (Figures Bx), the TIC-norm after a logarithmic intensity transformation (Figures Cx) and the TIC-norm after a square root transformation (Figures Dx).

FIGS. 10A1 to 10C3 show histograms of three uniformly distributed compounds of the rat testis after applying the TIC-norm with an exclusion list (Figures Ax), the TIC-norm after a square root intensity transformation (Figures Bx) and the TIC-norm after a logarithmic intensity transformation (Figures Cx).

FIG. 11A to 11F show distributions and correlation coefficients of normalization factors calculated from the rat testis dataset.

DETAILED DESCRIPTION

Figures 1A, 1B, 1C, 1D, 1E:
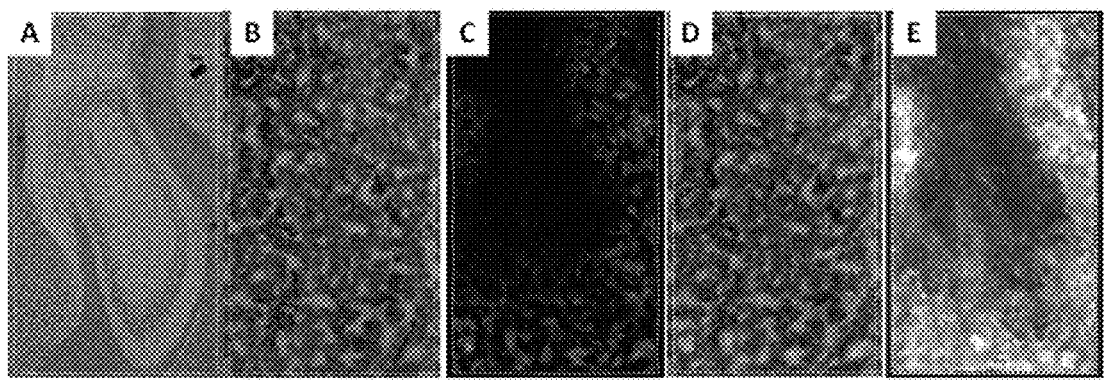
FIGS. 1A to 1E show different conventional images of a piece of rat hippocampus at 20 μm lateral resolution.

While the invention has been shown and described with reference to a number of embodiments thereof, it will be recognized by those skilled in the art that various changes in form and detail may be made herein without departing from the spirit and scope of the invention as defined by the appended claims.

The examples below show that normalization improves the amount of information extracted from mass spectrometric imaging data sets, especially for MALDI imaging when the lateral resolution approaches the level of the inhomogeneities of the matrix layer. The same may be true when other factors are present that influence the overall intensities of the measured mass spectra, such as different salt or lipid concentrations.

It is necessary to understand that certain assumptions are made on the data for all normalization approaches, e.g. that the integrated area of all peaks in the mass spectra should be comparable (in case of normalization on the TIC), that the overall intensities of the peaks should be rather similar (in case of the vector norm), that the noise level or median baseline should be similar for all peaks. In mass spectrometry-based serum profiling, where normalization on the TIC is usually used, it is assumed that only a few mass signals change throughout the dataset and that the majority of mass signals are constant. In the case of MALDI imaging of tissue sections, this assumption is often not justified because different protein profiles may be present in different regions of the tissue. If no normalization is applied, other assumptions are made on the data, namely that there are no effects such as inhomogeneous matrix layers or disturbing salt or lipid concentrations. The question whether any normalization at all or which normalization is warranted can be answered by determining which of the assumptions is most true.

As shown in the examples below, it may be necessary to perform normalization on mass spectrometric imaging data sets to get access to the true histological distribution of compounds, especially if the resolution of the MALDI imaging is comparable with the size of the matrix structures (crystals). However, if the known normalization on the TIC-norm or the vector norm is applied to mass spectra of MALDI imaging data sets of tissue sections, the mass images derived from normalized mass spectra can show strong artifacts. These artifacts result from an inhomogeneous distribution of compounds in the tissue section leading to aberrant mass signals with unusually high intensities or integrated areas and are particularly dangerous for the interpretation of the data, because they can accidentally reflect real histological differences in the tissue. It can be further observed that the normalization on the TIC is less prone to artifacts compared to the normalization on the vector norm.

The manual exclusion of the aberrant mass signals from calculating normalization factors solves the problem and results in mass images that reflect a true distribution of compounds. However, the disadvantage of this most reliable approach is that it normally requires manual interaction with the data. This requires that both the presence of the problem and those signals causing the problems have to be identified first. The presence of the problem can be spotted by the appearance of "holes" in the distribution of the noise or in the mass images of abundant (homogeneously distributed) mass signals. The aberrant signals can easily be spotted by looking into mass spectra at those regions.

The normalization on the median and the noise level are robust against the presence of aberrant mass signals. The mass images according to these normalizations look less smooth than the normalization on the TIC with an exclusion list. However, they do not require a manual interaction and are more robust. Therefore, they can be considered as preferred for a primary normalization. The normalization on the median and on the noise level gives similar results. Since the normalization on the median is less influenced by common processing steps in MALDI imaging such as binning or spectra smoothing, the normalization on the median is the most robust approach.

EXAMPLES

For the examples below, the work flow for acquiring a MALDI imaging data set of a tissue sample comprises the following steps:

(a) A tissue sample is cut into cryosections with a cryomicrotome. The tissue sections with a thickness of 10 μm are transferred onto conductive Indium-Tin-Oxide coated glass slides, vacuum-dried in a desiccator for a few minutes, and washed two times in 70% Ethanol and once in 96% Ethanol for one minute each. Subsequently, the sections are dried and stored under vacuum until the matrix is applied.

(b) The tissue sections are coated with a matrix by vaporizing a matrix solution with an ultrasonic nebulizer, for instance, according to U.S. Pat. No. 7,667,196 B2 (Schürenberg) and US 2008/0142703 A1 (Schürenberg).

(c) Spatially resolved mass spectra of the coated tissue sections are acquired by a time-of-flight mass spectrometer in the linear mode. For each pixel, 200 laser shots are accumulated at constant laser energy.

There are different ways to overlay an optical image of a tissue section with a mass image of the same or adjacent tissue section. Here, the MALDI imaging data set is acquired prior to the optical image. The matrix layer applied to the tissue section in step (b) is removed after the mass spectrometric image has been acquired in step (c). Then the tissue section is subjected to routine histologic staining, and the optical image is acquired.

Example 1

The dataset of example 1 covers a small region of a rat brain, containing part of the hippocampus. The MALDI imaging dataset was acquired at a lateral resolution of 20 μm with a CHCA matrix (alpha-Cyano-4-hydroxy-cinnamic acid). At this resolution, the structure of the matrix crystals tends to be in the same order of magnitude as the lateral resolution. A non-normalized image will therefore be an overlay of the matrix structure with the distribution of the selected compound.

FIGS. 1A to 1E show different images of a tissue section of a rat hippocampus. FIG. 1A shows an optical image of an unstained tissue section prior to the preparation of a matrix layer. FIG. 1B shows an optical scan of the matrix layer after preparation. FIG. 1C shows a mass image of a selected compound without any normalization. In FIG. 1D, the optical image of the matrix layer of FIG. 1B is overlaid with the mass image of FIG. 1C showing that the spatial distribution of the selected mass signal is highly effected by the structure of the matrix layer. FIG. 1E shows the same mass signal after normalization using the vector norm. It can be clearly seen that the distribution of the mass signal now appears much smoother. The mass image follows the histological structure of the tissue section much better and shows a rather uniform distribution outside the hippocampus.

Example 2

The dataset of example 2 is acquired from a tissue section of a mouse pancreas. The islets of Langerhans in the mouse pancreas are small glands in which insulin, glucagone and certain other peptide hormones are produced and excreted. The tissue section of the mouse pancreas is coated with sinapinic acid matrix.

Figure 2:
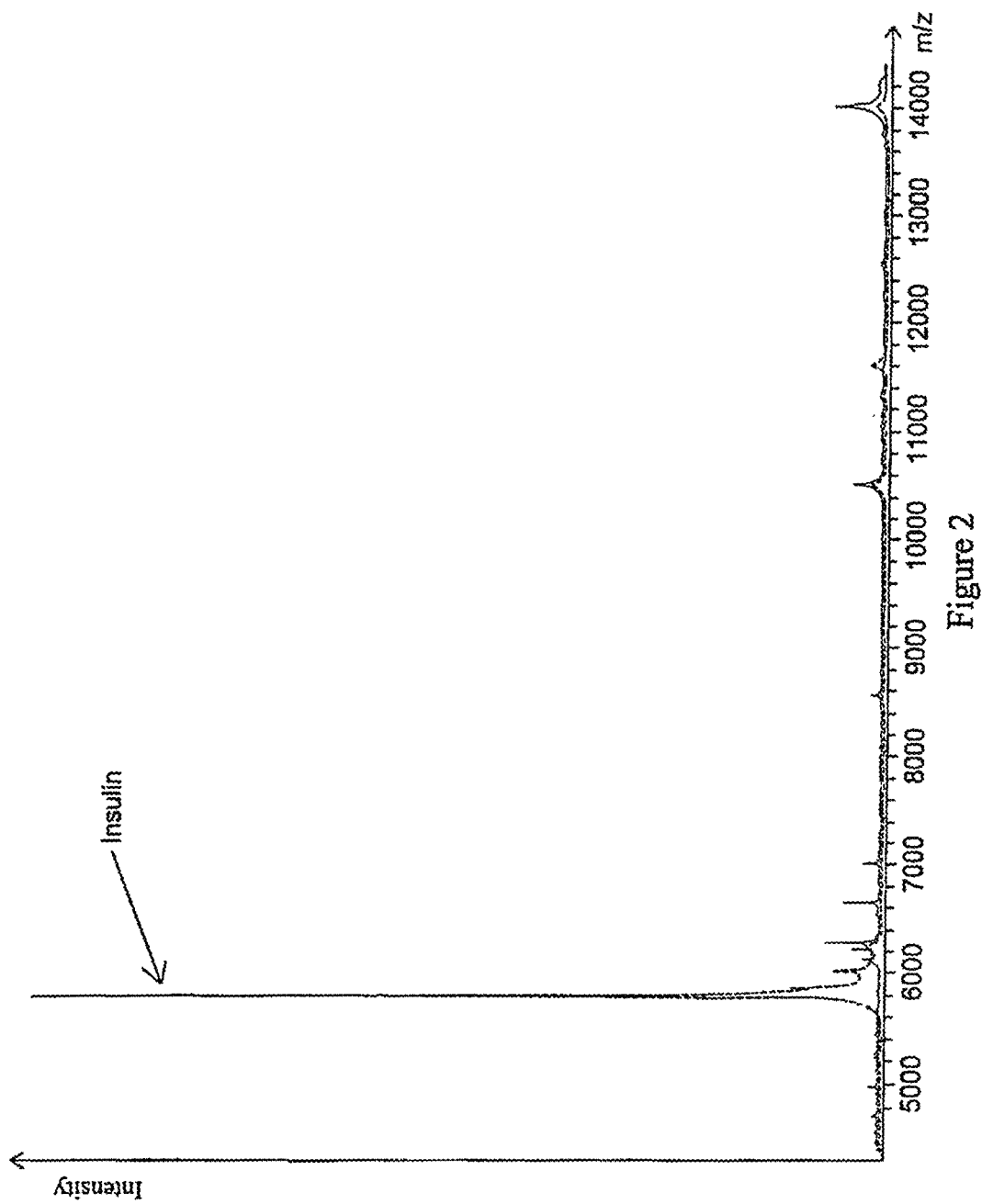
FIG. 2 shows averaged mass spectra acquired at one islet of Langerhans (dashed line, with an aberrant insulin peak) and at a "normal" area (solid line) of a mouse pancreas.

FIG. 2 shows averaged mass spectra from an islet of Langerhans (dashed line, with an aberrant insulin peak) and a different region of similar size (solid line) of the mouse pancreas. The intensities of insulin peaks are extremely high compared to other protein signals, while the remaining non-insulin signals show similar intensities in both regions. The insulin peaks reach intensities of up to 125 counts per laser shot, while the other signals are in the order of 1-2 counts per shot. This is an example for a spectrum in which one highly abundant peak is present in confined regions, being a particular problem for normalization of prior art.

FIG. 3 shows mass images of insulin (FIG. 3A to 3C) and of a homogeneously distributed protein (FIGS. 3D to 3F), each without normalization, with normalization on the vector norm and with normalization on the TIC. It becomes apparent, that the normalization on the vector norm leads to obvious artifacts. Both the spatial distribution and the intensity of the insulin signal appear inflated in the islets, while the homogeneously distributed protein appears to be absent. In contrast, the TIC-normalization is in a better agreement with the raw data. Only in one islet of Langerhans, an attenuation "hole" appears in the mass image of the homogeneously distributed protein. When the TIC-normalization is used with exclusion of the insulin signal (not shown), no holes are present in the mass image of the homogeneously distributed protein.

Example 3

The dataset of example 3 is acquired from a tissue section of a rat testis. There are seminiferous tubuli present in rat testis, in which the stem cells (spermatogonia) undergo maturation to mature spermatids. In a rat, 14 different stages can be defined. This process is highly structured and can appear at different stages of maturation in the same cross section The MALDI imaging dataset was acquired at a lateral resolution of 20 µm with a CHCA matrix (alpha-Cyano-4-hydroxy-cinnamic acid). The high spatial resolution is needed to resolve substructures in the tubuli. The drawback of CHCA matrix in linear mode is that it leads to quite broad mass signals.

Figure 4:
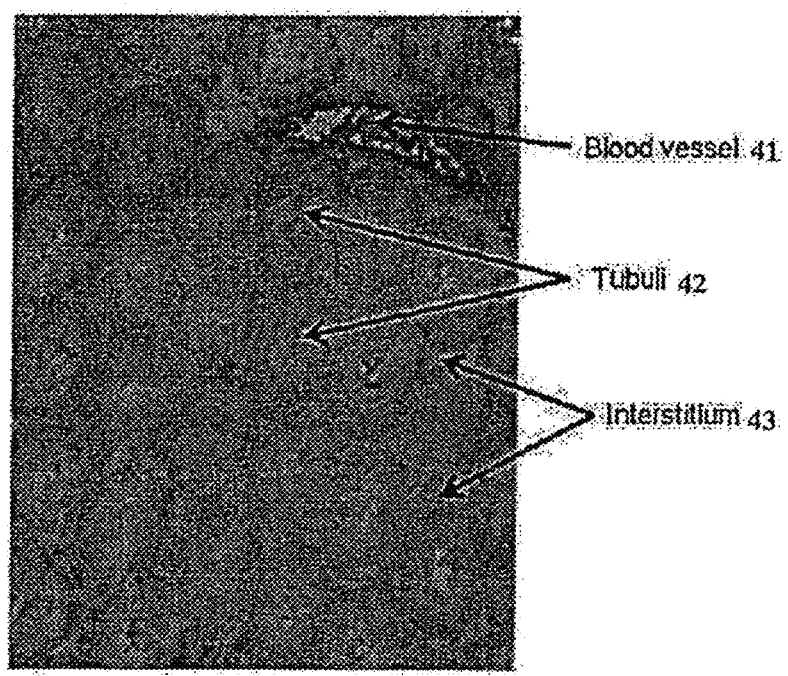
FIG. 4 shows an optical image after hematoxylin and eosin staining (H&E staining) of a tissue section of a rat testis.
Figure 5:
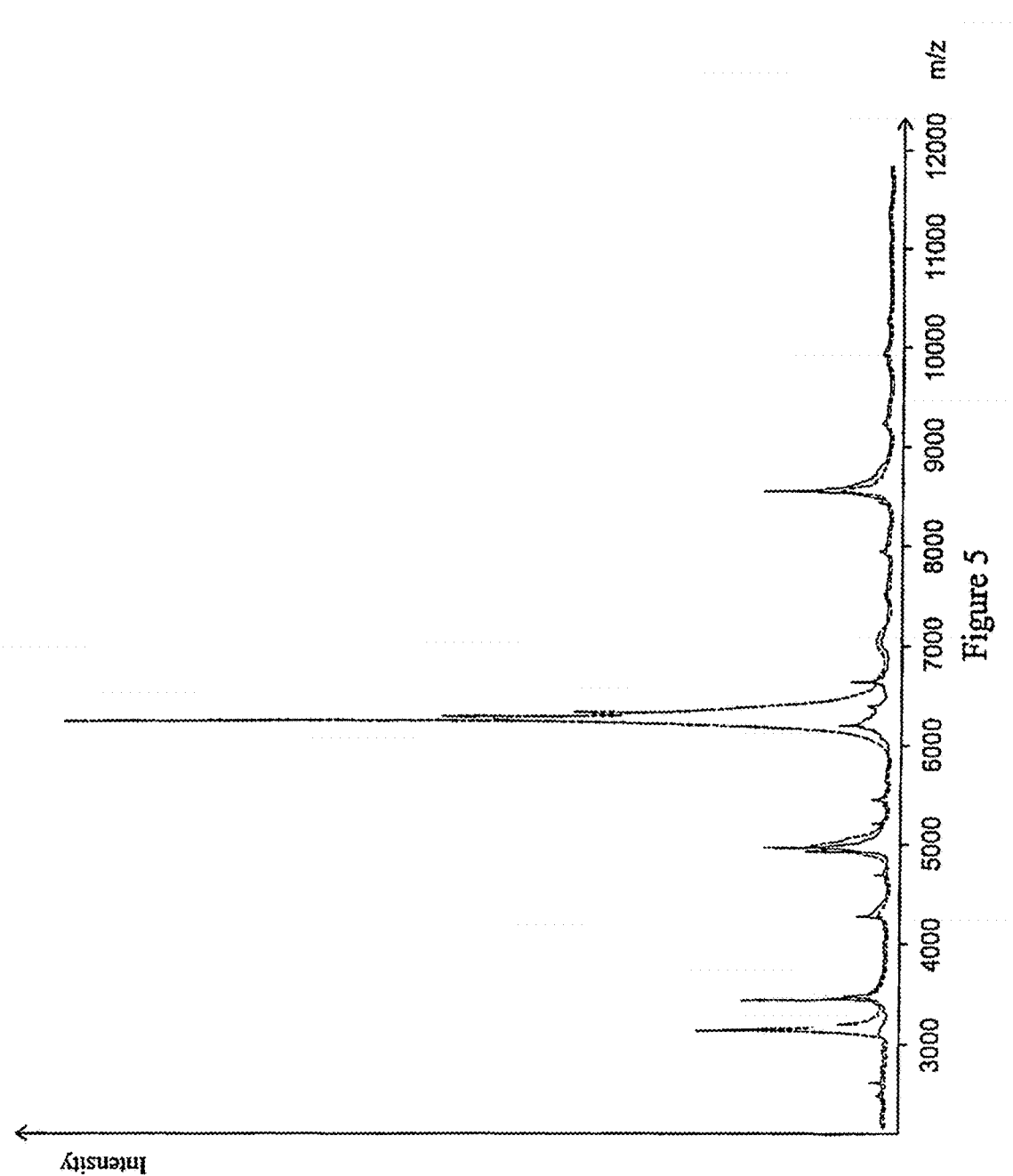
FIG. 5 shows averaged mass spectra acquired at a certain tubuli with an aberrant peak (dashed line) and at a "normal" tubuli (solid line) of the rat testis.

FIG. 4 shows a microscopic image after H&E staining of a tissue section of a rat testis. The optical image is obtained after MALDI imaging and shows the same region of the rat testis as the mass images of FIGS. 6A to 6F and FIGS. 7A to 7F. In the tissue section analyzed here, the cross-section through a blood vessel (41), cross-sections of seminiferous tubules (42) and the interstitium (43) are visible. The maturation of the spermatides takes place in the tubules. Different tubules can have different maturation states with differing molecular signals. In this tissue section, there is a group of tubules characterized by one aberrant mass signal at about 6263 Dalton (FIG. 5). This mass signal is not as intensive as that of insulin in the previous example, but it contains a comparably large area compared to the total area of the spectrum due to its width. Therefore it also affects the normalization on the TIC-norm.

Importantly, the highly abundant mass signals of the mouse pancreas and the rat testis are related to real histological structures (islets of Langerhans and immature tubuli). It is therefore easily possible in cases like these to accept a normalization artifact as biologically meaningful information. It is easily possible that a compound being present at the same abundance across the entire tissue shows a tissue specific distribution in a normalized mass image, which might be misinterpreted as regulated in spermatide maturation in the case of rat testis FIGS. 6A to 6F show mass images of a compound that is homogeneously distributed in the tissue section of the rat testis except for the blood vessel. The non-normalized mass image (FIG. 6A) shows mainly the spatial distribution of the matrix layer overlaid with the real distribution. Both the normalization on the vector norm and the TIC-norm (FIGS. 6B and 6C) produce the same kind of artifacts, namely a wrong down regulation of the respective mass signal in some of the tubuli. Again, this artifact is dangerous, because it shows a spatial distribution that is in agreement with histology.

In FIGS. 6D to 6F, mass images normalized according to the invention are shown: a normalization on the TIC with exclusion of the aberrant mass signal (FIG. 6D), the normalization on the median (FIG. 6E) and on the noise level (FIG. 6F). The mass images of the homogeneously distributed compound look almost identical for the median and the noise level and do not produce the artificial down regulation. The normalization on the TIC with manual exclusion of the aberrant mass signal shows however the smoothest distribution. This is consistently found for other masses as well.

FIGS. 7A to 7F show mass images of a compound that is mainly present in certain tubuli. However, it is also present in some of those tubuli showing the aberrant mass signal, and the respective mass signals are therefore attenuated.

By applying TIC normalization with exclusion of the aberrant signal (FIG. 7D) or normalization on median (FIG. 7E) and on the noise level (FIG. 7F), respectively, the mass signal is most abundant in the seminiferous tubules but still visible in the interstitium. As described above, normalization using the TIC-norm with manual exclusion is least affected by the distribution of the matrix crystals and shows the least noisy image. Without any normalization, it is not possible to detect the characteristic presence of this signal in the interstitium.

Figure 8:
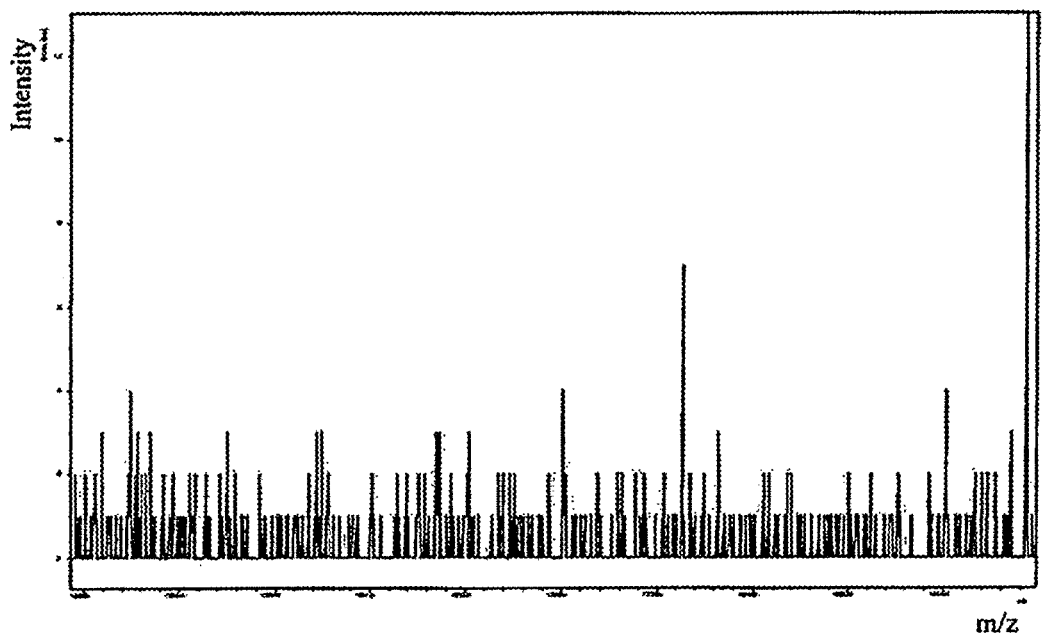
FIG. 8 shows a mass spectrum of low intensity wherein only the very upper part of the baseline is recorded or even only electronic spikes are present in the spectrum.

Ideally, a mass spectrum contains a complete baseline with symmetric noise. This is actually one of the implicit assumptions of normalization on the noise level or the median. There are different reasons, why this is not always true. For example, there may be very little matrix at a certain region, or part of the tissue may not have adhered properly at the support, or the detector settings of the instrument may cut off the lower part of the baseline. In such a case it is possible to observe spectra as the one shown in FIG. 8, where only the very upper part of the baseline is recorded or even only electronic spikes are present in the spectrum. Such mass spectra have a negative effect on many normalization approaches, because they have an artificially low TIC, noise level and median, the latter two can actually be zero or very close to zero, which will artificially increase such spectra after normalization. If median or noise level is zero, then the normalization will be undefined because of a division by zero. Therefore these mass spectra have to be excluded from normalization.

If a particular mass signal can be matched (according to mass) in two or more mass spectra from different tissue areas, this signal intensity is an estimation of the abundance of a compound. These estimates might contain errors resulting from random noise, different signal-to-noise ratios due to varying concentrations of the compound or electronic noise. The error can depend on the intensity. Any statistical model would either directly account for variances or would transform the data so that the variances are approximately equal for all peak intensity levels. Here, two different intensity transformations are applied prior to a normalization by the TIC-norm of the transformed mass spectra, namely the square root and the logarithmic transformation of the intensities values.

FIGS. 9A1 to 9D3 show mass images of three different compounds (peak 1, peak 2 and peak 3) after normalization applying TIC-normalization (Figures Ax), TIC-normalization with an exclusion list (Figures Bx), TIC-normalization after logarithmic intensity transformation (Figures Cx) and TIC-normalization after square root intensity transformation (Figures Dx).

As can be seen in FIGS. 9C1 to 9C3, the logarithmic transformation leads to a "flat" look of the normalized mass images with little structure, which makes this normalization not applicable for MALDI imaging. The few "bright" pixels in the mass images are a result of applying the logarithmic transformation on mass spectra with an incomplete noise as described above. The square root transformation (shown in FIGS. 9D1 to 9D3) leads to structured mass images, which show similar features than the TIC based normalization. Moreover, the square root transformation shows only very slight artifacts compared to the TIC based normalization. The resulting mass images show less dynamic range, which may be a problem in the assessment of relative intensity differences in a dataset.

FIGS. 10A1 to 10C3 show histograms of three uniformly distributed mass signals after normalization applying the TIC-norm with an exclusion list (Figures Ax), the TIC-norm after a square root intensity transformation (Figures Bx) and the TIC-norm after a logarithmic intensity transformation (Figures Cx). These mass signals show a skewed distribution with a tail to the high intensities after the TIC normalization (FIGS. 10A1 to 10A3). Only a few pixels show the highest intensities. To see the true structure of the data it is often necessary to set the maximum intensity threshold to a value between 50% and 70% of the maximum intensity. After the square root transformation (FIGS. 10B1 to 10B3), these signals show a much more symmetric distribution. The logarithmic transformation (FIGS. 10C1 to 10C3) results in a very narrow distribution with a very long tail which leads to the flat appearance of the mass images shown in FIGS. 9C1 to 9C3.

In many IMS datasets the described problems do not appear. In such cases, the normalization with the TIC-norm can be applied without restriction. Because TIC-normalization seems to be superior if applicable, it is desirable to have an automatic algorithm to detect if TIC normalization is applicable. The correlation of the normalization factors calculated by the median or noise level with the ones calculated by the TIC-norm can be one way to achieve an automatic testing.

FIG. 11 shows several correlations for the data set of the rat testis. Since the normalization on the TIC with exclusion of aberrant mass signals is most preferred, it is used as standard method for the comparison. With the exception of the square root transformation (FIG. 11F), the best correlation was observed with the median normalization factors (FIG. 11C). Therefore, it appears to be possible to use the correlation of a non-parametric normalization, like median or noise level, with the TIC-normalization without exclusion to define a threshold for the automatic detection of problems with the TIC-normalization.

Applied to MALDI imaging data sets of tissue sections, common normalization based on the vector norm and the TIC-norm can lead to artifacts. However, a normalization is necessary to deal with spatial inhomogeneities of the matrix layer. Although the normalization on the noise level, the median or the TIC after square root transformation can be used to get normalized mass images without artifacts, TIC normalization with a manual exclusion of mass signals causing the artifacts gives the best results. This approach often needs a manual intervention by the user.

In any case, care is needed when TIC normalization (without an exclusion list) is applied. The median normalization can be used as an additional tool to spot artifacts generated by TIC normalization. The comparison of the images after TIC normalization and median normalization is a good way to test the applicability of TIC normalization. If this comparison shows substantial differences in the resulting normalized mass images then TIC normalization should not be applied.

What is claimed is:

1. A method for determining the spatial distribution of a biomarker, drug or metabolite of a drug in a tissue with different types of cells, the method comprising:
   providing a section of the tissue;
   acquiring a set of mass spectra at a plurality of spatially-separated pixel locations of the tissue section;
   identifying mass ranges in the mass spectra that correspond to tissue compounds that are inhomogeneously distributed within the tissue section and produce mass signals with high intensity or large areas under the peak in confined regions of the tissue section;
   determining a p-norm of each of the mass spectra as transformed by the application of an intensity value exclusion list that suppresses the mass signals in the identified mass ranges;
   normalizing each mass spectrum using the p-norm determined for that mass spectrum; and
   deriving a mass image of the biomarker, drug or drug metabolite from the normalized mass spectra and determining the spatial distribution of the biomarker, drug or drug metabolite in the tissue.

2. The method according to claim 1, wherein the mass image is a first mass image and wherein the method further comprises:

(a) normalizing each mass spectrum by computing a p-norm of that mass spectrum without transformation of the mass spectrum by application of an exclusion list;

(b) deriving a second mass image of the biomarker, drug or drug metabolite from the mass spectra normalized in step (a); and (c) comparing the first and second mass images and determining the spatial distribution from the second mass image when the first and second mass images are substantially similar, otherwise determining the spatial distribution from the first mass image.

3. The method according to claim 1, wherein the mass spectra of the mass spectrometric imaging data set are acquired by MALDI imaging.

4. The method according to claim 1, wherein the p-norm is the total ion count.

5. The method according to claim 1, wherein the identified mass ranges of the exclusion list are such that the distribution of noise or the mass images of abundant and homogeneously distributed mass signals do not comprise holes in the mass spectra.

6. The method according to claim 1, wherein the mass signals of the exclusion list are predetermined according to tissue type.

7. The method according to claim 6, wherein the tissue comprises pancreatic tissue and the identified mass ranges of the exclusion list comprise a mass signal that corresponds to insulin and the confined regions of the tissue section comprise islets of Langerhans.

8. The method according to claim 6, wherein the tissue comprises brain tissue and the identified mass ranges of the exclusion list comprise mass signals of abundant beta-amyloid peptides.

9. The method according to claim 1, wherein the determined mass image of the biomarker, drug or drug metabolite is displayed.

10. A method for determining the spatial distribution of the kind or state of a tissue with different types of cells, the method comprising:

providing a section of the tissue;

acquiring a set of mass spectra at a plurality of spatially-separated pixel locations of the tissue section;

identifying mass ranges in the mass spectra that correspond to tissue compounds that are inhomogeneously distributed within the tissue section and produce mass signals with high intensity or large areas under the peak in confined regions of the tissue section;

determining a p-norm of each of the mass spectra as transformed by the application of an intensity value exclusion list that suppresses the mass signals in the identified mass ranges;

normalizing each mass spectrum using the p-norm determined for that mass spectrum; and deriving a mass image of the of the kind or state of the tissue by combining at least two different mass signals of the normalized mass spectra and determining the spatial distribution of the kind or state of the tissue from the mass image.

* * * * *